US007749551B2

(12) United States Patent
Sugimoto et al.

(10) Patent No.: US 7,749,551 B2
(45) Date of Patent: Jul. 6, 2010

(54) MINT COMPOSITION

(75) Inventors: Daisuke Sugimoto, Kanagawa (JP);
Yoshihiro Yaguchi, Kanagawa (JP);
Masaki Kumatani, Kanagawa (JP);
Makoto Emura, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 492 days.

(21) Appl. No.: 11/686,456

(22) Filed: Mar. 15, 2007

(65) Prior Publication Data
US 2007/0218178 A1  Sep. 20, 2007

(30) Foreign Application Priority Data
Mar. 16, 2006  (JP) .......................... P.2006-072039

(51) Int. Cl.
*A23L 1/22* (2006.01)
*A61K 36/534* (2006.01)
(52) U.S. Cl. ...................... 426/534; 424/747
(58) Field of Classification Search ................ 426/534; 424/737
See application file for complete search history.

(56) References Cited

U.S. PATENT DOCUMENTS 6,479,088 B1 * 11/2002 Johnson ...................... 426/492

FOREIGN PATENT DOCUMENTS

JP       59-42326       3/1984

OTHER PUBLICATIONS

Berger, R., et al., "Natural Occurrence of Undecaenes in Some Fruits and Vegetables", J. Food Science, vol. 50 (1985), pp. 1655-1667.
Berger, R., et al., "Novel Volatiles in Pineapple Fruit and Their Sensory Properties", J. Agric. Food Chem., vol. 33, No. 2 (1985), pp. 232-235.
Takeoka, G., et al., "Volatile Constituents of Pineapple", American Chemical Society, vol. 388 (1989), pp. 223-237.
Naef, R., et al., "Volatile Constituents in Extracts of Mandarin and Tangerine Peel", Journal of Essential Oil Research, vol. 13 (2001), pp. 154-157.
Fickert, et al., Lebensmittelchemie, vol. 53, No. 5 (1999), pp. 109-110.
Moore, R., et al., "Odoriferous C11 Hydrocarbons from Hawaiian Dictyopteris", Journal of Organic Chemistry, vol. 39, No. 15 (1974), pp. 2201-2207.
Marner, F., et al., "Synthese Isomerer 1,3,5,8-Undecatetraene", Liebigs Ann. Chem., (1982), pp. 579-584.
Huang, F., et al., "Changes of Aroma Constituents During Zuoquing Procedure and its Relation to Oolong Tea Quality", Journal of Tea Science, vol. 23, No. 1 (2003), pp. 31-37.
Jacobsen, C., et al., "Oxidation in Fish Oil-Enriched Mayonnaise", European Food Research Technology, vol. 211 (2000), pp. 86-98.
Beaulieu, J., et al. "Identification of Volatile Compounds in Cantaloupe at Various Developmental Stages Using Solid Phase Microextraction", Journal of Agricultural Food Chemistry, vol. 49 (2001), pp. 1345-1352.
Yamamoto, Y., "Neodictyoprolenol and Dictyoprolenol, the Possible Biosynthetic Intermediates of Dictyopterenes, In Japanese Brown Algae Dictyopteris", Journal of Biosciences, vol. 56, No. ½ (2001), pp. 6-12.
Fischer, N., "Flavor Components in Selected Exotic Fruits", Dragoco Report, (1966), pp. 137-147.
Japan Patent Office Gazette, "Known Customary Technologies (Perfume)," Part II, Flavor, published Jan. 14, 2000, pp. 476-495.

* cited by examiner

*Primary Examiner*—Keith D Hendricks
*Assistant Examiner*—Elizabeth Gwartney
(74) *Attorney, Agent, or Firm*—Fitzpatrick, Cella, Harper & Scinto

(57) ABSTRACT

The present invention relates to a mint composition, which comprises a mint substance and a 1,3,5,8-undecatetraene; and a fragrance-added or flavored product containing the mint composition. The mint composition has enhanced diffusing property and intensity of fragrance or flavor showing a high impact, shows excellent natural feeling and taste and also has excellent durability in fragrance or flavor.

15 Claims, No Drawings

MINT COMPOSITION

FIELD OF THE INVENTION

The present invention relates to a mint composition and to a product to which fragrance or flavor is imparted by the mint composition. More particularly, the invention relates to a mint composition which has enhanced diffusing property and intensity of mint-feeling fragrance or flavor, shows a strong impact, and is excellent in natural feeling and taste and durability of the mint-feeling fragrance or flavor, and to a product to which fragrance or flavor are imparted by the mint composition.

BACKGROUND OF THE INVENTION

As a result of diversification of various kinds of foods or beverages, fragrances or cosmetics, materials for health or hygiene, etc., in recent years, there has been new demands which have not been aimed until now for fragrance or flavor components used for imparting fragrance or flavor therefor. With regard to the fragrance or flavor components, there have been particular demands that they have strong impact, show unique fragrance or flavor with high taste and are highly compatible with other fragrance or flavor used together. Therefore, it has been a very important problem in a fragrance or flavor industry to develop fragrance or flavor materials satisfying the such requirements.

Particularly, as a result of an increase in orientation to nature by people, there has been a strong demand for the development of mint-feeling fragrance or flavor materials having fragrance or flavor whereby natural environment is characteristically imaged, being derived from a natural compound or composed of a compound which is same as or similar to a natural compound and having high safety, good taste and strong impact.

1,3,5,8-Undecatetraene has been found as a very minor constituent from fruits, brown algae, etc. (Non-Patent Documents 1 to 12) and its synthetic method has been known as well (Non-Patent Document 7). On the other hand, with regard to scent of 1,3,5,8-undecatetraene, it has been reported that, although the aroma reminds woody, it suggests the smell of sea water or sea algae and, as compared with 1,3,5,7-undecatetraene, it is inferior in view of scent (Patent Document 1).

Non-Patent Document 1: *J. Food Science*, Vol. 50, 1985, pages 1655 to 1667

Non-Patent Document 2: *J. Agric. Food Chem.*, Vo. 33, 1985, pages 232 to 235

Non-Patent Document 3: *ACS Symp. Ser. J.*, 388, 1989, pages 223 to 237

Non-Patent Document 4: *J. Essent. Oil Res.*, Vol. 13, 2001, pages 154 to 157

Non-Patent Document 5: *Lebensmittelchemie*, 53(5), 1999, pages 109 to 110

Non-Patent Document 6: *J. Org. Chem.*, Vol. 39, 1974, pages 2201 to 2207

Non-Patent Document 7: *Liebigs Ann. Chem.*, 1982, pages 579 to 584

Non-Patent Document 8: *Chaye Kexue*, 23(1), 2003, pages 31 to 37

Non-Patent Document 9: *European Food Research Technology*, 211, 2000, pages 86 to 98

Non-Patent Document 10: *J. Agric. Food Chem.*, Vol. 49, 2001, pages 1345 to 1352

Non-Patent Document 11: *J. Biosciences*, 56(1/2), 2001, pages 6 to 12

Non-Patent Document 12: *Dragoco Report*, 1966, pages 137 to 147

Patent Document 1: JP-A-59-42326

Non-Patent Document 13: Japan Patent Office Gazette, Known Customary Technologies (Perfume), Part II, Flavor, published on Jan. 14, 2000, pp. 476-495

SUMMARY OF THE INVENTION

An object of the present invention is to provide fragrance or flavor materials having high taste, showing excellent quality of fragrance or flavor and being useful for imparting fragrance or flavor, whereby demands for diversified products endowed with odor are able to be satisfied. A particular object of the present invention is to provide an improved mint composition having enhanced diffusing property and intensity of mint-feeling fragrance or flavor, showing a strong impact, and being excellent in natural feeling and taste and durability of mint-feeling fragrance or flavor.

A further object of the present invention is to provide a fragrance-added or flavored product containing the mint composition.

In order to achieve the above-mentioned objects, the present inventors have carried out the studies repeatedly. As a result, they have found that, when the aforementioned 1,3,5,8-undecatetraene, which has been believed to have inferior odor as compared with 1,3,5,7-undecatetraene, is contained in a mint substance, it is now possible to prepare a mint composition having mint-feeling fragrance or flavor which has enhanced diffusing property and intensity of fragrance or flavor making the impact stronger, has enhanced natural feeling and taste as well and is excellent in duration of fragrance or flavor as compared with the case where the mint substance is solely used. Based upon such findings, the present invention has been accomplished.

Namely, the present invention relates to the followings.

(1) A mint composition, which comprises a mint substance and a 1,3,5,8-undecatetraene.

(2) The mint composition according to (1), wherein the mint substance is at least one member selected from the group consisting of hakka (Japanese mint) oil, peppermint oil, spearmint oil, eucalyptus oil, menthol, menthone, methofuran, mentholactone, isomenthone, carvone, camphor, pulegol, pulegone, isopulegol, isopulegone and cineol.

(3) The mint composition according to (1), wherein the 1,3,5,8-undecatetraene is at least one of 1-(E,Z,Z)-3,5,8-undecatetraene and 1-(E,E,Z)-3,5,8-undecatetraene.

(4) The mint composition according to (1), wherein the 1,3,5,8-undecatetraene is contained in an amount of from 0.000001 to 1 part by weight with respect to 1 part by weight of the mint substance.

(5) The mint composition according to (1), which is for use in imparting fragrance or flavor.

(6) A fragrance-added or flavored product comprising the mint composition according to (1), said product being odor with the fragrance or flavor.

(7) The fragrance-added or flavored product according to (6), which is one member selected from the group consisting of oral composition, pharmaceutical, food or beverage, fragrance or cosmetic, daily goods or sundry.

As compared with the case of using the mint substance solely, the mint composition of the present invention has enhanced diffusing property and intensity of fragrance or flavor showing a high impact, shows a significantly good natural feeling and taste and also has durable mint-feeling fragrance or flavor.

Accordingly, utilizing the above-mentioned excellent characteristics, the mint composition of the present invention is capable of being effectively used as a material for imparting mint-feeling fragrance or flavor to various products such as oral composition, pharmaceutical, food or beverage, fragrance or cosmetic, daily goods or sundry.

In the fragrance-added or flavored product containing the mint composition of the present invention, diffusing property and intensity of fragrance or flavor are enhanced giving a strong impact, good mint-feeling fragrance or flavor having excellent natural feeling and taste are available and the above-mentioned excellent mint-feeling fragrance or flavor are durable for a long period.

DETAILED DESCRIPTION OF THE INVENTION

With regard to the mint substance used in the mint composition of the present invention, there is no particular limitation but anything may be used so far as it has been already used for imparting fragrance or flavor. Examples of the mint substance used in the present invention include hakka (Japanese mint) oil, peppermint oil, spearmint oil, eucalyptus oil, menthol, menthone, methofuran, mentholactone, isomenthone, carvone, camphor, pulegol, pulegone, isopulegol, isopulegone and cineol. With regard to the mint substance in the mint composition of the present invention, one of the members mentioned hereinabove may be used solely or two or more thereof may be used in combination depending upon the application, etc. Among them, in the mint composition of the present invention, one or more of hakka oil, peppermint oil, spearmint oil, menthol, menthone and carvone is preferably used as the mint substance in view of easy availability and high refreshing property.

With regard to the 1,3,5,8-undecatetraene used in the mint composition of the present invention, it has four double bonds, and therefore, eight geometrical isomers are present. To be more specific, there are eight isomers, which are 1-(E,E,E)-3,5,8-undecatetraene, 1-(E,E,Z)-3,5,8-undecatetraene, 1-(E,Z,E)-3,5,8-undecatetraene, 1-(E,Z,Z)-3,5,8-undecatetraene, 1-(Z,E,E)-3,5,8-undecatetraene, 1-(Z,E,Z)-3,5,8-undecatetraene, 1-(Z,Z,E)-3,5,8-undecatetraene and 1-(Z,Z,Z)-3,5,8-undecatetraene.

Each of these 1,3,5,8-undecatetraene is oily (liquid) at room temperature.

With regard to the 1,3,5,8-undecatetraene, any of the above-mentioned isomers may be used in the present invention and, among them, 1-(E,Z,Z)-3,5,8-undecatetraene and 1-(E,E,Z)-3,5,8-undecatetraene are preferably used in view of their excellent fragrance or flavor characteristics.

With regard to the 1,3,5,8-undecatetraene, the one which is prepared by extraction from natural substance may be used, the one which is prepared by means of chemical synthesis (such as that which is synthesized by the process mentioned in *Liebigs Ann. Chem.*, 1982, pages 579 to 584 (Non-Patent Document 7)) may be used or the one which is prepared from a natural substance and the one which is prepared by means of chemical synthesis may be used together. In the case by means of chemical synthesis, it is possible to prepare the 1,3,5,8-undecatetraene in large quantities.

There is no particular limitation for the method of preparation of the mint composition but any method by which a composition, in which the mint substance and the 1,3,5,8-undecatetraene are uniformly mixed, can be prepared may be adopted. Since both of the mint substance and the 1,3,5,8-undecatetraene are usually oily at room temperature, the mint composition of the present invention in which both are uniformly mixed is able to be prepared usually by a mere mixing of them at room temperature. However, the present invention is not limited thereto and it is also possible to prepare a mint composition, according to the necessity, by the use of a solvent such as ethanol, isopropanol, propylene glycol, dipropylene glycol, hexylene glycol, glycerol and triacetin.

The mint composition of the present invention may contain only two components which are the mint substance and the 1,3,5,8-undecatetraene or it may further contain other component(s).

When the mint composition of the present invention further contains other component(s), commonly-used fragrance or flavor component(s) which are other than the mint substance and the 1,3,5,8-undecatetraene may be contained therein.

When the mint composition of the present invention contains other fragrance or flavor component(s) together with the mint substance and the 1,3,5,8-undecatetraene, various kinds of synthetic aroma chemicals, natural essential oils, natural aroma chemicals, citrus fruit oils, animal aroma chemicals, etc. may be used within such an extent that no bad affection is resulted thereby on the characteristic of the mint composition of the present invention that "the composition has an impact, has excellent natural feeling and fragrance or flavor and has durable mint-feeling fragrance or flavor". For example, natural aroma chemicals, synthetic aroma chemicals, etc. mentioned in Japan Patent Office Gazette, Known Customary Technologies (Perfume), Part II, Flavor, published on Jan. 14, 2000, pp. 476-495 (Non-Patent Document 13) may be appropriately compounded therewith. Representative examples thereof to be used in the mint composition of the present invention include α-pinene, limonene, cis-3-hexenol, anethole, citral, citronellal, citronellol, linalool, eugenol, nonadienal, nonadienol, caryophyllene, anis essential oil, star anis oil, wintergreen oil, tea tree oil and lemon oil, and one or more thereof may be used.

The mint composition of the present invention may contain, according to the necessity, one or more fragrance- or flavor-retaining agent(s) which has/have been commonly used in fragrance or flavor compositions. Examples of the fragrance- or flavor-retaining agent include ethylene glycol, propylene glycol, dipropylene glycol, glycerol, hexylene glycol, benzyl benzoate, triethyl citrate, diethyl phthalate, Hercolyn, medium-chain fatty acid triglyceride and medium-chain fatty acid diglyceride and one or more thereof may be contained therein.

There is no particular limitation for the ratio of the 1,3,5,8-undecatetraene with respect to the mint substance contained in the mint composition of the present invention but the ratio may be adjusted depending upon the object of use, application, product, etc. of the mint composition. Usually, with respect to 1 part by weight of the mint substance, preferably 0.000001 to 1 part by weight of the 1,3,5,8-undecatetraene is contained, more preferably 0.000002 to 0.3 part by weight is contained and, still more preferably, 0.00001 to 0.1 part by weight is contained.

When the ratio of the mint substance and the 1,3,5,8-undecatetraene contained in the mint composition is set within the above-mentioned range, it is possible to give a mint composition having a strong impact, an excellent natural feeling and a durable and excellent mint-feeling fragrance or flavor.

The amounts of the mint substance and the 1,3,5,8-undecatetraene with respect to the total weight of the mint composition of the present invention are able to be adjusted by the factor whether other component(s) is/are present or, when other component(s) is/are contained, they are able to be adjusted by the type of fragrance or flavor or other component being compounded together, application and object of use of the mint composition, etc. When the mint composition of the present invention contains the mint substance and the 1,3,5,8-undecatetraene only, the mint substance is preferably contained in an amount of 50 to 99.9999% by weight, more preferably 70 to 99.9998% by weight or, particularly preferably, 90 to 99.999% by weight and the 1,3,5,8-undecatetraene is preferably contained in an amount of 50 to 0.0001% by weight, more preferably 30 to 0.0002% by weight or, particularly preferably, 10 to 0.001% by weight based on the total weight of the mint composition.

When the mint composition of the present invention contains other component(s) together with the mint substance and the 1,3,5,8-undecatetraene, the mint substance is preferably contained in an amount of 0.1 to 99.99% by weight, more preferably 1 to 99% by weight or, particularly preferably, 10 to 90% by weight and the 1,3,5,8-undecatetraene is preferably contained in an amount of 5 to 0.00001% by weight, more preferably 3 to 0.00002% by weight or, particularly preferably, 1 to 0.0001% by weight based on the total weight of the mint composition so as to impart mint-feeling fragrance or flavor to the product.

Representative examples of the fragrance-added or flavored containing the mint composition of the present invention include oral composition, pharmaceutical, food or beverage, fragrance or cosmetic, daily goods or sundry.

To be more specific, examples of the oral composition to which fragrance or flavor may be imparted by the mint composition of the present invention include dentifrice, oral washing agent, mouth wash, troche and chewing gum.

Examples of the pharmaceutical to which fragrance or flavor may be imparted by the mint composition of the present invention include skin external preparations such as cataplasma and ointment, and an oral medicine.

Examples of the food or beverage to which fragrance or flavor may be imparted by the mint composition of the present invention include food or beverage such as fruit juice beverage, fruit wine, carbonated beverages, soft beverage, drinking agent, milk beverage and the like beverages; and ice cream, sherbet, ice candy and the like frozen desserts; jelly, pudding and the like desserts; chocolate, chewing gum and the like Western-style confectioneries; yokan (sweet jelly of adzuki beans) and the like Japanese-style confectioneries; jam; candy; jasmine tea and the like herb teas.

Examples of the fragrance or cosmetic, daily goods or sundry to which fragrance or flavor may be imparted by the mint composition of the present invention include fragrance product, skin-care cosmetic, make-up cosmetic, hair cosmetic, anti-sunburn cosmetic, medicinal cosmetic, hair-care product, soap, body cleanser, bath agent, detergent, fabric softener, cleansing agent, kitchen detergent, bleaching agent, aerosol agent, deodorant and/or aromatizing agent, repellent and the like sundries.

To be more specific, the followings may be listed.

Examples of the fragrance product include perfume, eau de parfum, eau de toilette and eau de Cologne.

Examples of the skin-care cosmetic include face-washing cream, vanishing cream, cleansing cream, cold cream, massage cream, milky lotion, cosmetic lotion, beauty liquid, pack and make-up remover.

Examples of the make-up cosmetic include foundation, face powder, pressed powder, talcum powder, rouge, lipstick, lip cream, cheek rouge, eye liner, mascara, eye shadow, eyebrow-color, eye pack, nail enamel and enamel remover.

Examples of the hair cosmetic include pomade, brilliantine, set lotion, hair stick, hair solid, hair oil, hair treatment, hair cream, hair tonic, hair liquid, hair spray, bandolin, hair growth agent and hair dye.

Examples of the anti-sunburn cosmetic include suntan products and sunscreen products.

Examples of the medical cosmetic include antiperspirant, after-shaving lotion or gel, permanent wave agent, medical soap, medical shampoo and medical skin cosmetic.

Examples of the hair-care product include shampoo, rinse, two-in-one shampoo, conditioner, treatment and hair pack.

Examples of the soap include bath soap, scented soap, perfume soap, transparent soap and synthetic soap.

Examples of the body cleanser include body soap, body shampoo and hand soap.

Examples of the bath agent include bathing agent (such as bath salt, bath tablet and bath liquid), foam bath (such as bubble bath), bath oil (such as bath perfume and bath capsule), milk bath, bath jelly and bath cube.

Examples of the detergent include heavy duty detergent for clothing, light detergent for clothing, liquid detergent, laundry soap, compact detergent and powdery soap.

Examples of the fabric softener include softener and furniture care.

Examples of the cleansing agent include cleanser, house cleaner, toilet cleaner, both cleaner, glass cleaner, mold remover and waste pipe cleaner.

Examples of the detergent for kitchen include soap for kitchen, synthetic soap for kitchen and detergent for tableware.

Examples of the bleaching agent include oxidation type bleaching agent (bleaching agent of chlorine type and of oxygen type), reduction type bleaching agent (such as bleaching agent of sulfur type) and optical bleaching agent.

Examples of the aerosol agent include spray-type aerosol and powder spray aerosol.

Examples of the deodorant and/or aromatizing agent include solid type, gel type and liquid type.

Examples of the dairy goods or sundry include tissue and toilet paper.

When the mint composition of the present invention is used for imparting fragrance or flavor to various kinds of above-mentioned products, the mint composition may be directly added or applied to the product; the mint composition may be added or applied thereto after making it into liquid by dissolving, for example, in alcohol or polyhydric alcohol such as propylene glycol and glycerol; the mint composition may be added or applied thereto after dissolving or emulsifying and/or dispersing it by using natural gummy matters (such as gum arabic and tragacanth gum) or surfactant (such as nonionic surfactant [e.g., glycerol fatty acid ester and sucrose fatty acid ester], anionic surfactant, cationic surfactant and amphoteric surfactant); the mint composition may be added or applied thereto in a powdery form prepared by coating it with a filler such as natural gummy matters (e.g., gum arabic), gelatin and dextrin; or the mint composition may be added or applied thereto as microcapsules by treating it with a diluting agent, depending upon the type of the fragrance-added or flavored product or upon the final form of the product (product form such as liquid, solid, powder, gel, mist and aerosol).

It is also possible that the mint composition is used after making it stable thereby to be subsequently sustained and released by clathrating it in an clathrate agent such as cyclodextrin.

Amount of the mint composition to be added or applied to the product in conducting the impartment of fragrance or flavor is able to be adjusted depending upon type and form of the product, effect and action of imparting fragrance or flavor demanded by the product, amounts of the mint substance and the 1,3,5,8-undecatetraene in the mint composition, etc.

When the product to which fragrance or flavor may be imparted is food or beverage, oral composition, pharmaceutical, etc., amount of the mint composition with respect to the weight of the product is usually preferred to be about 0.0005 to 20% by weight and particularly preferred to be about 0.001 to 5% by weight.

In these products, it is preferred, in view of the above-mentioned excellent imparting effect of fragrance or flavor by the mint composition of the present invention, that the amount of the mint substance to be added or applied thereto is 0.001 to 1% by weight or, particularly, 0.01 to 0.5% by weight and the amount of the 1,3,5,8-undecatetraene to be added to applied thereto is 0.05 to 0.0000001% by weight or, particularly, 0.01 to 0.000001% by weight based on the weight of the product.

When the product to which fragrance or flavor may be imparted is fragrance product, skin-care cosmetic, make-up cosmetic, hair cosmetic, anti-sunburn cosmetic, medicinal cosmetic, hair-care product, soap, body cleanser, bath agent, detergent, fabric softener, cleansing agent, kitchen detergent, bleaching agent, aerosol agent, deodorant and/or aromatizing agent, daily goods or sundry, etc., amount of the mint composition of the present invention to be added or applied thereto may also be freely adjusted depending upon the effect and action expected for each of the products and it is usually preferred that the amount of the mint composition with respect to the weight of the product is about 0.001 to 25% by weight or, particularly, about 0.01 to 0.5% by weight.

At that time, it is preferred, in view of the above-mentioned excellent imparting effect of fragrance or flavor by the mint composition of the present invention, that the amount of the mint substance to be added or applied to the product is 0.001 to 1% by weight or, particularly, 0.01 to 0.5% by weight and the amount of the 1,3,5,8-undecatetraene to be added or applied to the product is 0.05 to 0.0000001% by weight or, particularly, 0.01 to 0.000001% by weight based on the weight of the above-mentioned product to which the mint composition is added or applied.

EXAMPLES

The present invention will now be specifically illustrated by the following Examples although the present invention is not limited by the following Examples at all. Instruments for the measurement and conditions for the measurement used in the following Examples will be shown below.

(1) Proton nuclear magnetic resonance spectrum ($^3$H-NMR);

Instrument: type DRX-500 (500 MHz) (manufactured by Bruker Bio-Spin GmbH)

Internal standard substance: tetramethylsilane (2) Infrared absorption spectrum (IR);

Instrument: Nicolet Avator 360 FR-IR (manufactured by Nicolet Japan K. K.)

Measuring method: film method (3) Mass spectrum (MS);

Instrument: GCMS-QP2010 mass spectrometer (ionization voltage: 27 eV) (manufactured by Shimadzu Corporation)

Synthetic Example 1

Production of (3E,5Z,8Z)-1,3,5,8-undecatetraene and (3E,5E,8Z)-1,3,5,8-undecatetraene Production was conducted by the process mentioned in *Liebigs Ann. Chem.*, 1982, pages 579 to 584 (Non-Patent Document 7). To be more specific, production was conducted by the following process.

(1) Production of 1-hexen-5-yn-3-ol:

(i) Metal aluminum (11.0 g, 410 mmol), 500 mg of mercury (II) chloride and 100 ml of diethyl ether were added to a reactor under a nitrogen atmosphere, 67.0 g (560 mmol) of 2-propyl bromide was dropped into the solution at 0° C. and, after completion of the dropping, the mixture was stirred at it was for 1.5 hours. The reaction solution was cooled down to −50° C., a mixed solution of 31.5 g (560 mmol) of acrolein and 50 ml of ethyl ether was dropped thereinto at −50° C. and, after that, the mixture was stirred at −50° C. for 1 hour. A 10% aqueous sulfuric acid (100 ml) and 100 ml of cold water were added thereto to stop the reaction followed by extracting with diethyl ether. The organic layer was washed with a saturated aqueous sodium carbonate solution and a saturated aqueous sodium chloride solution and dried over anhydrous magnesium sulfate. The solvent was evaporated and the resultant concentrate was distilled (at 50 to 52° C./12 Torr) to give 20.4 g (yield: 38%) of the target product.

(ii) Analytical result of the compound prepared in the above (i) by $^1$H-NMR and IR is as follows and the compound was confirmed to be 1-hexen-5-yn-3-ol.

$^1$H-NMR (CCl$_4$): δ=2.0 (t, 1H), 2.35 (dd, 2H), 3.77 (s, OH), 4.22 (dt, 1H), 5.0 to 6.2 (m, 3H)

IR (KBr): 3380, 3305, 3025, 2140, 1660, 725 cm$^{-1}$ (2) Production of 1-undecen-5,6-diyn-3-ol:

(i) Tetrahydrofuran (100 ml) and 13.4 g (540 mmol) of metal magnesium were added to a reactor under a nitrogen atmosphere and 60.0 g (550 mmol) of ethyl bromide was dropped thereinto to prepare a mixed solution (Grignard reagent). After that, a solution of 23.5 g (240 mmol) of 1-hexen-5-yn-3-ol dissolved in 50 ml of tetrahydrofuran was dropped thereinto followed by stirring at room temperature for 1 hour. Then 0.2 g of copper cyanide was added thereto and a solution of 36.0 g (240 mmol) of 2-pentynyl bromide dissolved in 50 ml of tetrahydrofuran was dropped thereinto followed by stirring for 12 hours more. A saturated aqueous ammonium chloride solution was added to stop the reaction followed by extracting with diethyl ether. The resulting organic layer was dried over anhydrous magnesium sulfate, the solvent was evaporated therefrom and the resultant concentrate was distilled (at 79 to 80° C./0.02 Torr) to give 27.2 g (yield: 70%) of the target product.

(ii) Analytical result of the compound prepared in the above (i) by $^1$H-NMR, IR and MS is as follows and the compound was confirmed to be 1-undecen-5,8-diyn-3-ol.

$^1$H-NMR (CCl$_4$): δ=1.13 (t, 3H), 2.15 (qt, 2H), 2.35 (dt, 2H), 3.1 (m, 3H), 4.2 (dt, 2H), 5.0 to 6.2 (m, 3H)

IR (KBr): 3380, 3090, 2975, 1440, 1340, 1155 cm$^{-1}$

MS: 162 (M$^+$), 105, 91, 57

(3) Production of (5Z,8Z)-1,5,8-undecatrien-3-ol (i) 1-Undecen-5,8-diyn-3-ol (10.0 g, 61.7 mmol), 45 ml of petroleum ether, 15 ml of acetone, 0.5 g of Lindlar catalyst and 0.01 g of 10% Pd/BaSO$_4$ were added to a reactor under a nitrogen atmosphere. After that, hydrogenation was carried out at room temperature and atmosphere pressure. After completion of the reaction, the catalysts were removed, the solvent was evaporated and the resultant concentrate was distilled (at 50° C./0.03 Torr) to give 7.7 g (yield: 75%) of the target product.

(ii) Analytical result of the compound prepared in the above (i) by $^1$H-NMR, IR and MS is as follows and the compound was confirmed to be (5Z,8Z)-1,5,8-undecatrien-3-ol.

$^1$H-NMR (CCl$_4$): δ=1.48 (t, 3H), 2.07 (q, 2H), 2.28 (t, 2H), 2.77 (t, 2H), 2.95 (s, 1H), 4.1 (m, 1H), 5.0 to 6.1 (m, 7H)

IR (KBr): 3360, 3080, 3020, 1660, 730 cm$^{-1}$

MS: 162 (M$^+$-H$_2$O), 110, 81, 57, 55

(4) Production of (3E,5Z,8Z)-1,3,5,8-undecatetraene and (3E,5E,8Z)-1,3,5,8-undecatetraene (i) (5Z,8Z)-1,5,8-undecatrien-3-ol (3.0 g, 18.1 mmol), 60 ml of hexamethylphosphoric triamide (HMPTA) and 16.4 g (36.2 mmol) of methyl(triphenoxy)phosphonium iodine (MTPI) were added to a reactor under a nitrogen atmosphere followed by stirring at room temperature for 3 hours and at 50° C. for 1 hour. The reaction was stopped by addition of 50 ml of ice water followed by extracting with pentane. After the organic layer was washed with a saturated aqueous sodium chloride solution, it was dried over anhydrous magnesium sulfate. After evaporation of the solvent, the resulting residue was subjected to a chromatographic treatment using pentane to give 2.0 g (yield: 74%) of a crude product. The resultant crude product (0.5 g, 3.37 mmol) was further purified by a chromatography using pentane and diethyl ether to give 0.05 g (yield: 20%) of (3E,5Z,8Z)-1,3,5,8-undecatetraene and 0.05 g (yield: 20%) of (3E,5E,8Z)-1,3,5,8-undecatetraene.

(ii) Analytical result of the compounds prepared in the above (i) by $^1$H-NMR, IR and MS is as follows and the compounds were confirmed to be (3E,5Z,8Z)-1,3,5,8-undecatetraene and (3E,5E,8Z)-1,3,5,8-undecatetraene.

(3E,5Z,8Z)-1,3,5,8-undecatetraene:

$^1$H-NMR (CCl$_4$): δ=1.0 (t, 3H), 2.07 (q, 2H), 2.92 (t, 2H), 5.0 to 6.7 (m, 9H)

IR (KBr): 3080, 3010, 2860, 1690, 750 cm$^{-1}$

MS: 148 (M$^+$), 119, 105, 91, 79

(3E,5E,8Z)-1,3,5,8-undecatetraene:

$^1$H-NMR (CCl$_4$): δ=1.0 (t, 3H), 2.05 (q, 2H), 2.85 (t, 2H), 4.9 to 6.7 (m, 9H)

IR (KBr): 3080, 3000, 2870, 1630, 730 cm$^{-1}$

MS: 148 (M$^+$), 105, 105, 91, 79

Synthetic Example 2

Production of (3Z,5E,8Z)-1,3,5,8-undecatetraene (1) Production of (2E)-octen-5-yn-1-ol:

Diethyl ether (200 ml) and 4.0 g (105.3 mmol) of lithium aluminum hydride were added to a reactor under a nitrogen atmosphere, a solution of 15.0 g (123 mmol) of 2,5-octadiyn-1-ol dissolved in 100 ml of diethyl ether was dropped thereinto and, after that, the mixture was stirred at room temperature for 5 hours. Ice water was added thereto and then a 2N aqueous hydrochloric acid solution was added there to stop the reaction followed by extracting with ethyl ether. The organic layer was dried over anhydrous magnesium sulfate, the solvent was evaporated and the resultant concentrate was distilled (at 55° C./0.05 Torr) to give 11.4 g (yield: 75%) of the target product.

(ii) Analytical result of the compound prepared in the above (i) by $^1$H-NMR, IR and MS is as follows and the compound was confirmed to be (2E)-octen-5-yn-1-ol.

$^1$H-NMR (CCl$_4$): δ=1.1 (t, 3H), 2.13 (qd, 2H), 2.85 (m, 2H), 4.2 (s, 1H), 5.65 (m, 2H)

IR (KBr): 3350, 3030, 2920, 1685, 970 cm$^{-1}$

MS: 124 (M$^+$), 109, 95, 79, 77

(2) Production of (2E,5Z)-2,5-octadien-1-ol:

(i) Raney nickel (0.01 g), 150 ml of ethanol, 0.33 ml (5.0 mmol) of ethylenediamine and 10.0 g (80.6 mmol) of (2E)-2-octen-5-yn-1-ol were added to a reactor under a nitrogen atmosphere. After that, hydrogenation was carried out at room temperature and atmosphere pressure. After completion of the reaction, the catalyst was removed, the solvent was evaporated and the resultant concentrate was distilled (at 92 to 93° C./12 Torr) to give 8.2 g (yield: 81%) of the target product.

(ii) Analytical result of the compound prepared in the above (i) by $^1$H-NMR, IR and MS is as follows and the compound was confirmed to be (2E,5Z)-2,5-octadien-1-ol.

$^1$H-NMR (CCl$_4$): δ=0.95 (t, 3H), 2.05 (q, 2H), 2.75 (m, 2H), 3.97 (m, 2H), 4.08 (s, 1H), 5.38 to 5.6 (m, 4H)

IR (KBr): 3330, 3010, 2880, 1685, 730 cm$^{-1}$

MS: 126 (M$^+$), 95, 93, 67, 41

(3) Production of (2E,5Z)-2,5-octadienetriphenyl phosphonium bromide:

Triphenyl phosphine (11.0 g, 42 mmol) and 100 ml of benzene were added to a reactor under a nitrogen atmosphere and a mixed solution of 6.56 g (41 mmol) of bromine and 25 ml of benzene was dropped thereinto. After that, a solution of 5.0 g (39.7 mmol) of (2E,5Z)-2,5-octadien-1-ol dissolved in 20 ml of benzene was dropped thereinto followed by stirring at room temperature for 2 hours. Then a mixed solution of 11.0 g (42 mmol) of triphenyl phosphine and 20 ml of benzene was added thereto and the mixture was heated to reflux for 4 hours and stirred at room temperature for 12 hours. The crystals were filtered and washed with benzene to give 13.9 g (yield: 78%) of the target product.

(4) Production of (3Z,5E,8Z)-1,3,5,8-undecatetraene:

(2E,5Z)-2,5-Octadienetriphenyl phosphonium bromide (10.0 g, 22.2 mmol) and 100 ml of tetrahydrofuran were added to a reactor under a nitrogen atmosphere. N-Butyl lithium (a 0.5N solution in pentane) (44.4 ml, 22.2 mmol) was dropped thereinto followed by stirring at room temperature for 30 minutes. A mixed solution of 1.24 g (22.2 mmol) of acrolein and 10 ml of tetrahydrofuran (10 ml) was dropped thereinto, the mixture was stirred at room temperature for 30 minutes and the reaction was stopped by addition of ice water thereto. It was extracted with diethyl ether and the organic layer was washed with a saturated aqueous sodium chloride solution and dried over anhydrous magnesium sulfate. After evaporating the solvent, the resultant concentrate was subjected to a chromatography treatment using pentane to obtain 0.72 g of crude product. The crude product thus obtained was dissolved in 5 ml of tetrahydrofuran, 0.45 g of tetracyanoethylene was added thereto and the mixture was stirred at room temperature for 5 hours. The residue prepared by concentrating the solvent was purified by chromatography to give 0.35 g (yield: 11%) of the target product.

(ii) Analytical result of the compound prepared in the above (i) by $^1$H-NMR, IR and MS is as follows and the compound was confirmed to be (3Z,5E,8Z)-1,3,5,8-undecatetraene.

$^1$H-NMR (CCl$_4$): δ=0.95 (t, 3H), 2.03 (q, 2H), 2.85 (t, 2H), 4.95 to 7.0 (m, 9H)

IR (KBr): 3080, 3010, 2960, 1620, 1005, 975, 730 cm$^{-1}$

MS: 148 (M$^+$), 119, 105, 91, 79

Example 1

Mint Composition (1) Menthone (manufactured by Takasago International Corporation) was used as a mint substance and 99.99 parts by weight of menthone was mixed, at room temperature, with 0.01 part by weight of (3E,5E,8Z)-1,3,5,8-undecatetraene produced in the above Synthetic Example 1 (Experiment No. (1a)), with 0.01 part by weight of (3E,5Z,8Z)-1,3,5,8-undecatetraene produced in the above Synthetic Example 1 (Experiment No. (1b)) or with a 1:1 (ratio by weight) mixture of (3E,5E,8Z)-1,3,5,8-undecatetraene and (3E,5Z,8Z)-1,3,5,8-undecatetraene produced in Synthetic Example 1 (Experiment No. (1c)). Thus, three kinds of mint compositions (menthone compositions) were prepared.

(2) Fragrance or flavor of the mint compositions (menthone compositions) prepared in the above (1) was evaluated by ten professional panelists according to the evaluating criteria shown in the following Table 1 where the fragrance or flavor of the menthone itself immediately after taken out from a tightly closed container was adopted as a standard (point 3) and the mean value thereof was adopted whereupon the result was as shown in the following Table 2. Incidentally, the points in Table 2 were the results of rounding off the first decimal place of the mean value.

(3) Evaluation of durability of fragrance or flavor in the mint substance (menthone) or mint composition (menthone composition) was conducted in such a manner that, in Experiment No. (1d) (menthone only), menthone was taken out into the air from the tightly closed container and allowed to stand for 3 hours at room temperature (25° C., 55% RH), the fragrance or flavor at that time was evaluated by ten professional panelists according to the evaluating criteria shown in the following Table 1 where the fragrance or flavor of the menthone itself immediately after taken out from a tightly closed container was adopted as a standard (point 3) and the mean value was adopted.

In the case of mint compositions (menthone compositions) (Experiment Nos. (1a), (1b) and (1c)), the evaluation was conducted in such a manner that the fragrance or flavor upon being allowed to stand for 3 hours at room temperature (25° C., 55% RH) the same as above immediately after preparation of the mint composition (menthone composition) was evaluated by ten professional panelists according to the evaluating criteria shown in the following Table 1 based on the fragrance or flavor of menthone itself immediately after taking out from the tightly closed container (point 3) and the mean value thereof was adopted (by rounding off the first decimal place of the mean value).

TABLE 1

Evaluating Criteria for Mint-Feeling Fragrance or Flavor

| | |
|---|---|
| Point 5 | As compared with the standard [1], diffusing property and intensity of fragrance or flavor were greatly enhanced showing a strong impact and, further, as compared with the standard [1], natural feeling and taste were also greatly enhanced showing very good mint-feeling fragrance or flavor. |
| Point 4 | As compared with the standard [1], diffusing property and intensity of fragrance or flavor were enhanced showing an impact and, further, as compared with the standard [1], natural feeling and taste were also enhanced showing good mint-feeling fragrance or flavor. |

TABLE 1-continued

Evaluating Criteria for Mint-Feeling Fragrance or Flavor

| | |
|---|---|
| Point 3 | (standard [1]) |
| Point 2 | As compared with the standard [1], diffusing property and intensity of fragrance or flavor were somewhat weak showing a decreased impact and, further, as compared with the standard [1], the resulting mint-feeling fragrance or flavor was with somewhat inferior natural feeling and taste. |
| Point 1 | As compared with the standard [1], diffusing property and intensity of fragrance or flavor were considerably weak showing no impact and, further, as compared with the standard [1], the resulting mint-feeling fragrance or flavor was with considerably inferior natural feeling and taste. |

[1] Standard: Fragrance or flavor of a mint substance itself or a mint composition immediately after the manufacture containing a mint substance and containing no 1,3,5,8-undecatetraene (a mint composition which was tightly closed and preserved immediately after its manufacture).

TABLE 2

| | Experiment Nos. | | | |
|---|---|---|---|---|
| | (1a) (EI) | (1b) (EI) | (1c) (EI) | (1d) (EC) |
| * Formulation (in part(s) by weight) | | | | |
| Mint substance | | | | |
| Menthone | 99.99 | 99.99 | 99.99 | 99.99 |
| * 1,3,5,8-Undecatetraene | | | | |
| 1,3,5,8-Undecatetraene mixture [1] | 0.01 | | | |
| (3E,5E,8Z)-1,3,5,8-Undecatetraene | | 0.01 | | |
| (3E,5Z,8Z)-1,3,5,8-Undecatetraene | | | 0.01 | |
| Fragrance or Flavor Property | | | | |
| Immediately after manufacture | 5 | 5 | 5 | 3 |
| Allowed to stand for 3 hrs after manufacture (evaluation for durability) | 5 | 5 | 5 | 1 |

[1] a 1:1 (ratio by weight) mixture of (3E,5E,8Z)-1,3,5,8-undecatetraene and (3E,5Z,8Z)-1,3,5,8-undecatetraene
EI: Example of the Invention
EC: Example for Comparison It will be noted from the result of the above Table 2 that the mint compositions of the present invention in Experiment Nos. (1a), (1b) and (1c) where a 1,3,5,8-undecatetraene was contained in a mint substance (menthone) had a strong impact and had a good mint-feeling fragrance or flavor having far better natural feeling and showed better durability for the fragrance or flavor as compared with a sole mint substance (menthone) (Experiment No. 1d).

Example 2

Mint Composition (an Example where a Mint Substance Other than Menthone was Used)

(1) Carvone (manufactured by Takasago International Corporation) was used as a mint substance and 99.98 parts by weight of carvone was mixed, at room temperature, with 0.02 part by weight of (3E,5E,8Z)-1,3,5,8-undecatetraene produced in the above Synthetic Example 1 (Experiment No. (2a)], with 0.02 part by weight of (3E,5Z,8Z)-1,3,5,8-undecatetraene produced in the above Synthetic Example 1 (Experiment No. (2b)) or with a 1:1 (ratio by weight) mixture of (3E,5E,8Z)-1,3,5,8-undecatetraene and (3E,5Z,8Z)-1,3,5,8-undecatetraene produced in Synthetic Example 1 (Experiment No. (2c)). Thus, three kinds of mint compositions (carvone compositions) were prepared.

(2) Fragrance or flavor of the mint compositions (carvone compositions) prepared in the above (1) were evaluated by ten professional panelists according to the evaluating criteria shown in the above Table 1 where the fragrance or flavor of the carvone itself immediately after taken out from a tightly-closed container was adopted as a standard (point 3) and the mean value was adopted whereupon the result was as shown in the following Table 3.

(3) Evaluation of durability of fragrance or flavor in the mint substance (carvone) or mint composition (carvone composition) was conducted in such a manner that, in Experiment No. (2d) (carvone only), carvone was taken out into the air from the tightly closed container and allowed to stand for three hours at room temperature (25° C., 55% RH), the fragrance or flavor at that time was evaluated by ten professional panelists according to the evaluating criteria shown in the above Table 1 where the fragrance or flavor of the carvone itself immediately after taken out from a tightly closed container was adopted as a standard (point 3) and the mean value was adopted.

In the case of mint compositions (carvone compositions) (Experiment Nos. (2a), (2b) and (2c)), the evaluation was conducted in such a manner that the fragrance or flavor upon being allowed to stand for 3 hours at room temperature (25° C., 55% RH) the same as above immediately after preparation of the mint composition (carvone composition) was evaluated by ten professional panelists according to the evaluating criteria shown in the above Table 1 based on the fragrance and/or flavor of carvone itself immediately after taking out from the tightly closed container (point 3) and the mean value thereof was adopted (by rounding off the first decimal place of the mean value).

better natural feeling and showed better durability for the fragrance or flavor as compared with a sole mint substance (carvone) (Experiment No. (2d)).

Example 3

Mint Composition (1) The components shown in the following Table 4 were mixed in the ratios shown in Table 4 at room temperature (25° C., 55% RH) to prepare mint compositions (Experiment Nos. (3a) and (3b)).

(2) Fragrance or flavor of the mint compositions prepared in the above (1) was evaluated in terms of points by ten professional panelists according to the evaluation criteria shown in the above Table 1 based on the fragrance or flavor of the mint composition (containing no 1,3,5,8-undecatetraene) of Experiment No. (3b) immediately after the manufacture (point 3) and mean values thereof were adopted to show the result of the following Table 4.

(3) Evaluation of durability of fragrance or flavor of a mint composition was conducted in such a manner that fragrance or flavor of each mint composition being allowed to stand for 3 hours in the air at room temperature (25° C., 55% RH) was evaluated in terms of points by ten professional panelists according to the evaluating criteria according to the above Table 1 based on a product prepared by preserving a part of the mint composition (a mint composition containing no 1,3,5,8-undecatetraene) of Experiment No. (3b) prepared in the above (1) in a tightly closed container (where fragrance and/or flavor was almost unchanged from the composition immediately after the manufacture) and then the mean value of the points was adopted.

TABLE 3

| | Experiment Nos. | | | |
|---|---|---|---|---|
| | (2a) (EI) | (2b) (EI) | (2c) (EI) | (2d) (EC) |
| *Formulation (in part(s) by weight) | | | | |
| Mint substance | 99.98 | 99.98 | 99.98 | 100.0 |
| * 1,3,5,8-Undecatetraene | | | | |
| 1,3,5,8-Undecatetraene mixture [1] | 0.02 | | | |
| (3E,5E,8Z)-1,3,5,8-Undecatetraene | | 0.02 | | |
| (3E,5Z,8Z)-1,3,5,8-Undecatetraene | | | 0.02 | |
| Fragrance or Flavor Property | | | | |
| Immediately after manufacture | 5 | 5 | 5 | 3 |
| After being allowed to stand for 3 hrs after manufacture (evaluation for durability) | 5 | 5 | 5 | 1 |

[1] a 1:1 (ratio by weight) mixture of (3E,5E,8Z)-1,3,5,8-undecatetraene and (3E,5Z,8Z)-1,3,5,8-undecatetraene
EI: Example of the Invention
EC: Example for Comparison It will be noted from the result of the above Table 3 that the mint compositions of the present invention in Experiment Nos. (2a), (2b) and (2c) where a 1,3,5,8-undecatetraene was contained in a mint substance (carvone) had a strong impact and had a good mint-feeling fragrance or flavor having far

TABLE 4

| | Expt. No. (3a) (EI) | Expt. No. (3b) (EC) |
|---|---|---|
| Formulation (in part(s) by weight) | | |
| * Mint substance | | |
| Peppermint oil | 20 | 20 |
| 1-Menthol | 40 | 40 |
| Spearmint oil | 10 | 10 |
| 1-Carvone | 23 | 23 |
| * 1,3,5,8-Undecatetraene [1] (as a 0.1% ethanolic solution) | 10 | — |
| * Other components | | |
| Anethole | 6 | 6 |
| Lemon oil | 1 | 1 |
| Ethanol | — | 10 |
| Fragrance or Flavor Property | | |
| Immediately after manufacture | 5 | 3 |
| After being allowed to stand for 3 hrs after manufacture (evaluation for durability) | 5 | 2 |

[1] A 0.1% ethanolic solution of (3E,5Z,8Z)-1,3,5,8-undecatetraene
EI: Example of the invention
EC: Example for comparison It will be noted from the result of the above Table 4 that the mint composition of the present invention of Experiment No. (3a) containing 1,3,5,8-undecatetraene together with a mint substance had enhanced diffusing property and taste of the mint-feeling fragrance or flavor giving a strong impact, had a far better natural feeling and showed better durability of the mint-feeling fragrance or flavor as compared with the mint composition of Experiment No. (3b) containing no 1,3,5,8-undecatetraene.

Example 4

Tooth Paste (1) Tooth paste was prepared according to the formulation shown in the following Table 5 using the mint composition containing the 1,3,5,8-undecatetraene prepared in Experiment No. (3a) of Example 3. To be more specific, all amounts of the components constituting the formulation for the tooth paste shown in Table 5 were mixed, stirred until they became uniform to prepare the tooth paste (Experiment No. (4A)).

(2) A tooth paste was prepared in the same manner as in the above (1) according to the tooth paste formulation shown in the following Table 5 using a mint composition containing no 1,3,5,8-undecatetraene prepared in Experiment No. (3b) of Example 3 (Experiment No. (4B)).

TABLE 5

|  | Expt. No. (4A) (EI) | Expt. No. (4B) (EC) |
|---|---|---|
| Formulation of tooth paste (part(s) by weight) |  |  |
| Calcium hydrogen phosphate | 51.0 | 51.0 |
| Glycerol | 26.0 | 26.0 |
| Sodium laurate | 1.4 | 1.4 |
| Sodium carboxymethyl cellulose | 1.0 | 1.0 |
| Sodium saccharine | 0.15 | 0.15 |
| Sodium benzoate | 0.05 | 0.05 |
| * Mint substance |  |  |
| 3a [1] | 1.0 | — |
| 3b [2] | — | 1.0 |
| Pure water | 19.4 | 19.4 |
| Total | 100 | 100 |

[1] The mint composition produced in Experiment No. (3a) containing (3E,5Z,8Z)-1,3,5,8-undecatetraene
[2] The mint composition produced in Experiment No. (3b) containing no 1,3,5,8-undecatetraene
EI: Example of the invention
EC: Example for comparison (3) The tooth paste of the example of the present invention of Experiment No. (4A) prepared in the above (1) had a fresh and natural mint-feeling fragrance or flavor where diffusing property and taste were enhanced, impact was strong and natural feeling and taste were good.

On the contrary, the tooth paste of Experiment No. (4B) prepared in the above (2) was insufficient in diffusing property of mint-feeling fragrance or flavor and inferior in fresh feeling and natural feeling to the product of Experiment No. (4A).

Example 5

Chewing Gum (1) Chewing gums were prepared according to the formulations shown in the following Table 6 using the mint composition (a mint composition containing a 1,3,5,8-undecatetraene) prepared in Experiment No. (3a) or the mint composition (a mint composition containing no 1,3,5,8-undecatetraene) prepared in Experiment No. (3b) of Example 3. To be more specific, all amounts of the components constituting the chewing gum formulation shown in the following Table 6 were mixed to manufacture a chewing gum.

TABLE 6

|  | Expt. No. (5A) (EI) | Expt. No. (5B) (EC) |
|---|---|---|
| Formulation for chewing gum (part(s) by weight) |  |  |
| Gum base | 24.0 | 24.0 |
| Corn syrup | 6.7 | 6.7 |
| Glycerol | 1.1 | 1.1 |
| Sugar | 67.0 | 67.0 |
| Mint composition |  |  |
| 3a [1] | 1.0 | — |
| 3b [2] | — | 1.0 |
| Pure water | 0.2 | 0.2 |
| Total | 100 | 100 |

[1] The mint composition produced in Experiment No. (3a) containing (3E,5Z,8Z)-1,3,5,8-undecatetraene
[2] The mint composition produced in Experiment No. (3b) containing no 1,3,5,8-undecatetraene
EI: Example of the invention
EC: Example for comparison The result was that the chewing gum of the example of the present invention of Experiment No. (5A) prepared in the above had a fresh and natural mint-feeling fragrance or flavor where diffusing property and taste were enhanced, impact was strong and natural feeling and taste were good.

On the contrary, the chewing gum of Experiment No. (5B) prepared in the above was insufficient in diffusing property of mint-feeling fragrance or flavor and inferior in fresh feeling and natural feeling to the product of Experiment No. (5A).

As compared with the case of the sole mint substance, the mint composition of the present invention has enhanced diffusing property and intensity of fragrance or flavor showing a high impact, shows excellent natural feeling and taste and also has excellent durability in fragrance and flavor. Accordingly, utilizing the above-mentioned excellent characteristics, the mint composition of the present invention may be effectively used as a material for imparting mint-feeling fragrance or flavor to various products such as oral composition, pharmaceutical, food or beverage, fragrance or cosmetic, daily goods or sundry.

While the invention has been described in detail and with reference to specific embodiments thereof, it will be apparent to one skilled in the art that various changes and modifications can be made therein without departing from the scope thereof.

This application is based on Japanese patent application No. 2006-072039 filed Mar. 16, 2006, the entire contents thereof being hereby incorporated by reference.

Further, all references cited herein are incorporated in their entireties.

What is claimed is:

1. A mint composition, which comprises a mint substance and a 1,3,5,8-undecatetraene.

2. The mint composition according to claim 1, wherein the mint substance is at least one member selected from the group consisting of Japanese mint oil, peppermint oil, spearmint oil, eucalyptus oil, menthol, menthone, methofuran, mentholactone, isomenthone, carvone, camphor, pulegol, pulegone, isopulegol, isopulegone and cineol.

3. The mint composition according to claim 1, wherein the 1,3,5,8-undecatetraene is at least one of 1-(E,Z,Z)-3,5,8-undecatetraene and 1-(E,E,Z)-3,5,8-undecatetraene.

4. The mint composition according to claim 1, wherein the 1,3,5,8-undecatetraene is contained in an amount of from 0.000001 to 1 part by weight with respect to 1 part by weight of the mint substance.

5. A method of imparting fragrance or flavor to a substance selected from the group consisting of an oral composition, pharmaceutical, food, beverage, fragrance and cosmetic, which comprises incorporating into said substance the mint composition according to claim 1.

6. A fragrance-added or flavored product selected from the group consisting of an oral composition, pharmaceutical, food, beverage, fragrance and cosmetic, said product comprising the mint composition according to claim 1.

7. The mint composition according to claim 2, wherein the 1,3,5,8-undecatetraene is at least one of 1-(E,Z,Z)-3,5,8-undecatetraene and 1-(E,E,Z)-3,5,8-undecatetraene.

8. The mint composition according to claim 2, wherein the 1,3,5,8-undecatetraene is contained in an amount of from 0.000001 to 1 part by weight with respect to 1 part by weight of the mint substance.

9. The mint composition according to claim 3, wherein the 1,3,5,8-undecatetraene is contained in an amount of from 0.000001 to 1 part by weight with respect to 1 part by weight of the mint substance.

10. The mint composition according to claim 7, wherein the 1,3,5,8-undecatetraene is contained in an amount of from 0.000001 to 1 part by weight with respect to 1 part by weight of the mint substance.

11. The mint composition according to claim 4, wherein the 1,3,5,8-undecatetraene is 1-(E,E,Z)-3,5,8-undecatetraene.

12. The mint composition according to claim 8, wherein the 1,3,5,8-undecatetraene is 1-(E,E,Z)-3,5,8-undecatetraene.

13. The mint composition according to claim 9, wherein the 1,3,5,8-undecatetraene is 1-(E,E,Z)-3,5,8-undecatetraene.

14. The mint composition according to claim 10, wherein the 1,3,5,8-undecatetraene is 1-(E,E,Z)-3,5,8-undecatetraene.

15. A method of imparting fragrance or flavor to a substance selected from the group consisting of an oral composition, pharmaceutical, food, beverage, fragrance and cosmetic, which comprises incorporating into said substance the mint composition according to claim 2.

\* \* \* \* \*